United States Patent
Scherer et al.

(10) Patent No.: US 9,012,851 B2
(45) Date of Patent: Apr. 21, 2015

(54) OPTICAL CHAMBER MODULE ASSEMBLY

(75) Inventors: James J. Scherer, Hillsborough, CA (US); Joshua B. Paul, Palo Alto, CA (US); Hans-Juerg Jost, Mountain View, CA (US)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 107 days.

(21) Appl. No.: 13/825,377

(22) PCT Filed: Sep. 9, 2011

(86) PCT No.: PCT/US2011/051100
§ 371 (c)(1),
(2), (4) Date: Mar. 21, 2013

(87) PCT Pub. No.: WO2012/050696
PCT Pub. Date: Apr. 19, 2012

(65) Prior Publication Data
US 2013/0175450 A1 Jul. 11, 2013

Related U.S. Application Data

(60) Provisional application No. 61/393,032, filed on Oct. 14, 2010.

(51) Int. Cl.
*G01J 5/08* (2006.01)
*G01N 21/61* (2006.01)
*G01N 21/3504* (2014.01)

(52) U.S. Cl.
CPC ............ *G01N 21/61* (2013.01); *G01N 21/3504* (2013.01)

(58) Field of Classification Search
CPC .......................................................... G01J 5/08
USPC .......................................................... 250/353
See application file for complete search history.

(56) References Cited

U.S. PATENT DOCUMENTS

| 4,627,067 A | 12/1986 | Barr, Jr. et al. |
| 4,749,276 A | 6/1988 | Bragg et al. |

(Continued)

OTHER PUBLICATIONS

Mark G. Allen, "Diode Laser Absorption Sensors for Gas Dynamic and Combustion Flows," Measurement Science and Technology (1998), http://www.iop.org/Journals/mt, pp. 1-61.

(Continued)

*Primary Examiner* — David Porta
*Assistant Examiner* — Hugh H Maupin
(74) *Attorney, Agent, or Firm* — Thomas F. Cooney; Gordon Stewart; Pamela Lau Kee

(57) ABSTRACT

A gas sensor system includes a laser module, optical chamber module, and a gas sensor cell. The laser chamber module includes two laser light sources producing laser light emissions at wavelengths $\lambda_1$ and $\lambda_2$, respectively. Each beam path optionally includes an optical isolator. The beam paths enter the housing of the optical chamber module where they are combined into a third wavelength, $\lambda$. The housing of the optical chamber module includes an inlet and an outlet for passing a selected target gas. The gas sensor cell mates to the inlet of the housing. The target gas passes through the adjacent gas cell and into the optical chamber module through the inlet. The target gas exits the optical chamber module through the outlet. Within the optical chamber module, a nonlinear crystal receives the laser light emissions at wavelengths $\lambda_1$ and $\lambda_2$ and generates the third wavelength, $\lambda_3$. The wavelength $\lambda_3$ is selected to be at the mid-IR spectral absorption feature of the target gas, i.e. a strong absorption line in the vibrational spectrum of a specific chemical species that is targeted by the gas sensor. The third wavelength $\lambda_3$ is generated by the interaction of the electric fields of the two laser emissions. The nonlinear optical crystal may be periodically poled, and configured to frequency-convert the first and second laser beams. The residual light from the two laser sources is removed from the mid-infrared beam with an absorptive and/or reflective optical filter.

21 Claims, 3 Drawing Sheets

(56) References Cited

U.S. PATENT DOCUMENTS

| | | | |
|---|---|---|---|
| 5,331,409 A | | 7/1994 | Thurtell et al. |
| 5,400,173 A | | 3/1995 | Komine |
| 5,577,061 A | | 11/1996 | Hasenberg et al. |
| 5,912,910 A | * | 6/1999 | Sanders et al. ............... 372/22 |
| 6,064,488 A | | 5/2000 | Brand et al. |
| 6,134,004 A | | 10/2000 | Reagen et al. |
| H1965 H | | 6/2001 | Burns et al. |
| 6,344,648 B1 | * | 2/2002 | Boucher et al. ............... 250/343 |
| 7,050,170 B2 | | 5/2006 | Chilese et al. |
| 7,154,595 B2 | | 12/2006 | Paldus et al. |
| H2197 H | | 8/2007 | Gord et al. |
| 7,265,842 B2 | | 9/2007 | Paldus et al. |
| 7,535,573 B2 | | 5/2009 | Kachanov et al. |
| 7,646,485 B2 | | 1/2010 | Tan |
| 7,810,376 B2 | | 10/2010 | Koulikov |
| 2002/0177248 A1 | | 11/2002 | McCann et al. |
| 2003/0202550 A1 | | 10/2003 | Goyal et al. |
| 2005/0077028 A1 | | 4/2005 | Oikawa |
| 2005/0225840 A1 | | 10/2005 | Drasek et al. |
| 2005/0226296 A1 | | 10/2005 | Botez et al. |
| 2005/0243876 A1 | * | 11/2005 | Kung ............... 372/21 |
| 2006/0011844 A1 | | 1/2006 | Oka et al. |
| 2006/0025835 A1 | | 2/2006 | Calcott |
| 2006/0245461 A1 | | 11/2006 | Islam |
| 2007/0076209 A1 | | 4/2007 | Baer et al. |
| 2007/0081162 A1 | | 4/2007 | Roller et al. |
| 2007/0133625 A1 | | 6/2007 | Ahn et al. |
| 2007/0133626 A1 | | 6/2007 | Ahn et al. |
| 2009/0028193 A1 | | 1/2009 | Islam |
| 2009/0028197 A1 | | 1/2009 | Arnone et al. |
| 2009/0296743 A1 | | 12/2009 | Islam |
| 2009/0304034 A1 | | 12/2009 | Mirov et al. |
| 2010/0053720 A1 | | 3/2010 | Magari et al. |
| 2010/0111122 A1 | | 5/2010 | Pushkarsky et al. |
| 2010/0163733 A1 | * | 7/2010 | Prasad et al. ............... 250/345 |
| 2010/0329291 A1 | | 12/2010 | Sanders |
| 2012/0287418 A1 | | 11/2012 | Scherer et al. |
| 2013/0044323 A1 | | 2/2013 | Liu et al. |

OTHER PUBLICATIONS

Douglas J. Bamford et al., "Widely tunable rapid-scanning mid-infrared laser spectrometer for industrial gass process stream analysis," Applied Optics, vol. 46 (19), pp. 3958-3968, (2007).

Weidong Chen et al., "Continuous-wave mid-infrared laser sources based on difference frequency generation," C R Physique (2007), doi:10.1016/j.crhy.2007.09.011, pp. 1-22.

T. Kelz et al., "Detection of CO in Air Using Diode Laser Pumped Difference-Frequency Generation in a Modular Setup," J. Quant. Spectrosc. Radiat. Transfer vol. 61 (5), pp. 591-601, (1999).

Anatolyi A. Kosterov et al., "Thermoelectrically cooled quantum-cascade-laser-based sensor for the continuous monitoring of ambient atmospheric carbon monoxide," Applied Optics, vol. 41 (6), pp. 1169-1173 (2002).

D. G. Lancaster et al., "Real-time measurements of trace gases using a compact difference-frequency-based sensor operating at 3.5 µm," Appl. Phys. B 67, pp. 339-345, (1998).

D. G. Lancaster et al., "Portable fiber-coupled diode-laser-based sensor for multiple trace gas detection," Appl. Phys. B 69, pp. 459-465, (1999).

D. Richter et al., "Tunable, fiber coupled spectrometer based on difference-frequency generation in periodically poled lithium niobate," Advanced Solid State Lasers, M. Fejer, H. Injeyan, and U. Keller, eds., vol. 26 of OSA Trends in Optics and Photonics (Optical Society of America, 1999), paper WC5., p. 1-4.

F. K. Tittel et al., "Novel Diode Laser-Based Sensors for Gas Sensing Applications," Laser Physics, vol. 10, No. 1, (2000), pp. 348-354.

Thomas Topfer et al., "Room-temperature mid-infrared laser sensor for trace gas detection," Applied Optics, vol. 36, (30), pp. 8042-8049, (1997).

M. Erdelyi et al., $^{13}CO_2/^{12}CO_2$ isotopic ratio measurements using a difference frequency-based sensor operating at 4.35 µm, Appl. Phys. B 75, pp. 289-295 (2002).

K. Fradkin et al., "Tunable midinfrared source by difference frequency generation in bulk periodically poled $KTiOPO_4$," Applied Physics Letters, vol. 74 (7), pp. 914-916, (1999).

D. Mazzotti et al., "Difference-frequency radiation around 4.3 µm for high sensivity and sub-Doppler spectroscopy of $CO_2$," Advanced Semiconductor Lasers and Their Applications (ASLA 1999), vol. 31 of OSA Trends in Optics and Photonics Series (TOPS), pp. 122-127.

K. P. Petrov et al., "Detection of CO in air by diode-pumped 4.6-µm difference-frequency generation in quasi-phase-matched $LiNbO_3$," Optics Letters, vol. 21 (1), pp. 86-88, (1996).

D. Richter et al., "Compact mid-infrared trace gas sensor based on difference-frequency generation of two diode lasers in periodically poled $LiNbO_3$," Appl. Phys. B 67, pp. 347-350, (1998).

Non-Final Office Action in companion U.S. Appl. No. 13/229,511, mailed Oct. 21, 2014.

* cited by examiner ions at wavelengths $\lambda_1$ and $\lambda_2$, respectively. Each beam path optionally includes an optical isolator. The beam paths enter the housing of the optical chamber module where they are combined into a third wavelength, $\lambda$. The housing of the optical chamber module includes an inlet and an outlet for passing a selected target gas. The gas sensor cell mates to the inlet of the housing. The target gas passes through the adjacent gas cell and into the optical chamber module through the inlet. The target gas exits the optical chamber module through the outlet.

OPTICAL CHAMBER MODULE ASSEMBLY

CROSS REFERENCE TO RELATED APPLICATIONS

This application is related to, and claims, under 35 U.S.C. 119(e), the benefit of the filing date of U.S. Provisional application No. 61/393,032, in the names of inventors James J. Scherer and Joshua B. Paul, filed Oct. 14, 2010 and titled "Single Frequency Tunable Middle Infrared Laser". This application is also related to co-pending U.S. patent application Ser. No. 13/229,511 titled "High-Accuracy Mid-IR Laser-Based Gas Sensor" in the names of the inventors of the instant application and filed on even date herewith. The aforementioned co-pending applications are hereby incorporated by reference herein in their entirety as if set forth fully herein.

BACKGROUND

Single frequency near-IR lasers are used in chemical sensors to produce desired wavelengths at the vibrational bands of a target sample. As many chemical species have low optical absorptivity in this region, systems using sensors based on conventional laser light sources are not particularly sensitive when combined with simple direct absorption approaches. System sensitivity can be improved by using elaborate and less robust spectroscopic approaches. To illustrate, the sensitivity of near-IR chemical sensors may be increased using ultra-long path astigmatic Herriott cells, resonant photo-acoustic approaches, or optical cavity-based methods, e.g. cavity ring-down spectroscopy (CRDS) and integrated cavity output spectroscopy (ICOS).

Photo-acoustic spectroscopy, while capable of extreme sensitivity, frequency requires the use of complicated resonant cells. In addition, the relative intensities of spectra using photo-acoustic spectroscopy can be difficult to interpret due to the variation in coupling of the optical excitation of the surrounding gases.

Astigmatic, multi-pass cells are relatively large, alignment-sensitive, and susceptible to mirror contamination.

Optical cavity based approaches are even more susceptible to mirror contamination, because they explicitly extract their sensitivity from the ultra high reflectivity of the cavity optics (R=99.9-99.99% typically). Additionally, CRDS is extremely alignment sensitive. ICOS, and particularly "off-axis" ICOS, requires relatively large sample cells, e.g. 2" diameter optics, which increases sample cell volume, pumping requirements, and overall system size. Even larger optics are required when extending this technique to the mid-IR range, further increasing cell volume.

SUMMARY

A gas sensor system includes a laser module, optical chamber module, and a gas sensor cell. The laser chamber module includes two laser light sources producing laser light emissions at wavelengths $\lambda_1$ and $\lambda_2$, respectively. Each beam path optionally includes an optical isolator. The beam paths enter the housing of the optical chamber module where they are combined into a third wavelength, $\lambda$. The housing of the optical chamber module includes an inlet and an outlet for passing a selected target gas. The gas sensor cell mates to the inlet of the housing. The target gas passes through the adjacent gas cell and into the optical chamber module through the inlet. The target gas exits the optical chamber module through the outlet.

Within the optical chamber module, a nonlinear crystal receives the laser light emissions at wavelengths $\lambda_1$ and $\lambda_2$ and generates the third wavelength, $\lambda_3$. The wavelength $\lambda_3$ is selected to be at the mid-IR spectral absorption feature of the target gas, i.e. a strong absorption line in the vibrational spectrum of a specific chemical species that is targeted by the gas sensor. The third wavelength, $\lambda_3$ is generated by the interaction of the electric fields of the two laser emissions. The nonlinear optical crystal may be periodically poled, and configured to frequency-convert the first and second laser beams. The residual light from the two laser sources is removed from the mid-infrared beam with an absorptive and/or reflective optical filter. The filter may comprise an optical bandpass or edge filter that transmits the light of wavelength $\lambda_3$ while rejecting the light of wavelength $\lambda_1$ and the light of wavelength $\lambda_2$. Alternatively, the filter may be a piece of polished germanium (with or without a dielectric coating to enhance the reflectivity of $\lambda_1$ and $\lambda_2$), or a transmissive optical substrate with a dielectric coating on one or both surfaces to reflect the two laser source wavelengths and transmit the wavelength $\lambda_3$. The filter 85 may also be wedged to further reduce optical fringing between the input optical face and output optical face of the filter. In this illustrative embodiment, the wedge may be from about 3° to about 5°.

DETAILED DESCRIPTION

Figure 1:
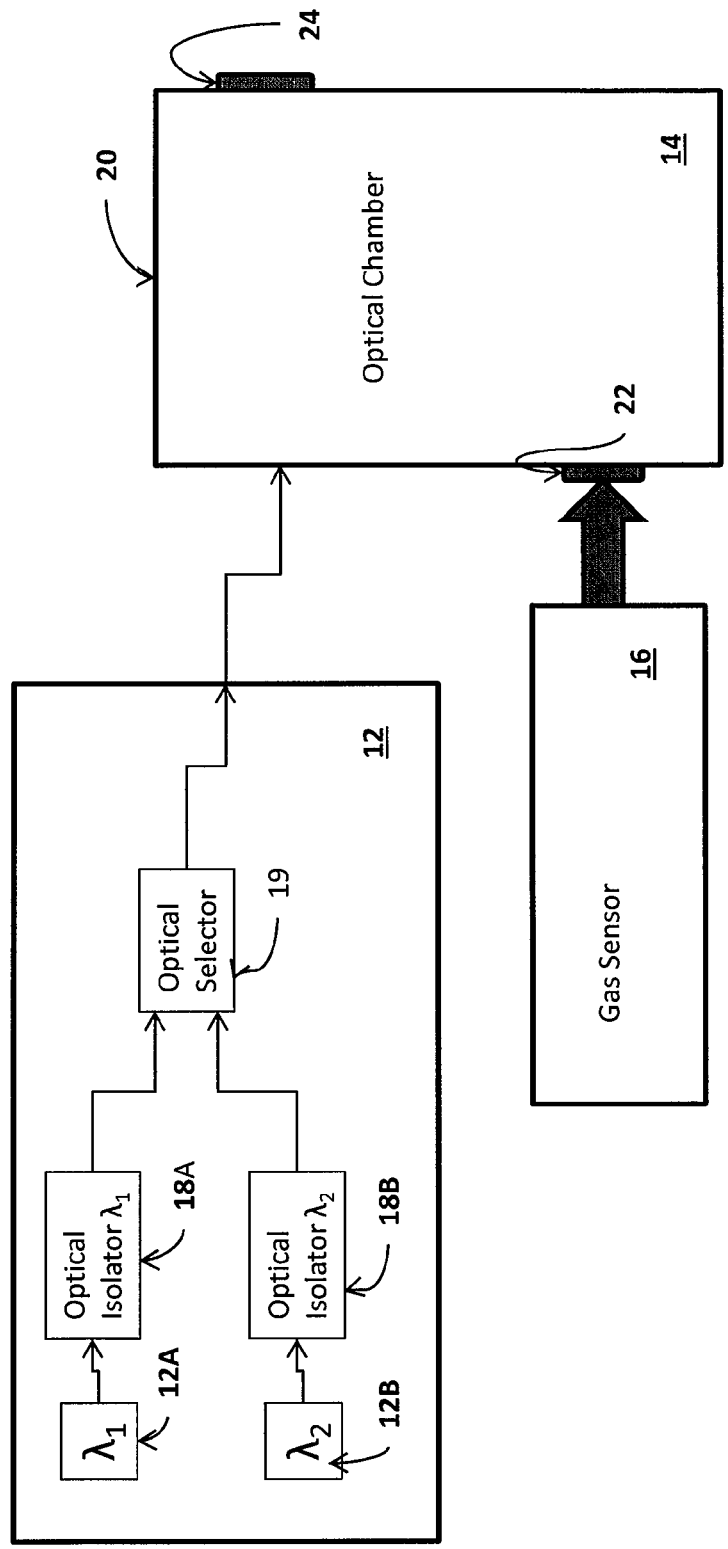
FIG. 1 shows a block diagram of the laser light system.

FIG. 1 is a block diagram for a gas sensor system 10 using a laser chamber module 12, an optical chamber module 14, and a gas sensor cell 16. The system is capable of sensing chemical species via fundamental vibrational bands in the middle IR region of the electromagnetic spectrum.

The laser chamber module 12 includes two laser light sources 12A, 12B producing laser light emissions at wavelengths $\lambda_1$ and $\lambda_2$, respectively. Each beam path optionally includes an optical isolator 18A, 18B. The beam paths enter an optical beam selector 19, i.e. a multiplexer. The selected beam path enters the housing 20 of the optical chamber module 14 where they are combined into a third wavelength, $\lambda_3$. The housing 20 includes an inlet 22 and an outlet 24 for passing a selected target gas. The gas sensor cell 12 mates to the inlet of the housing 22. The target gas passes through the adjacent gas cell 16 and into the optical chamber module 14 through the inlet 22. The target gas exits the optical chamber module 14 through the outlet 24.

Figure 2:
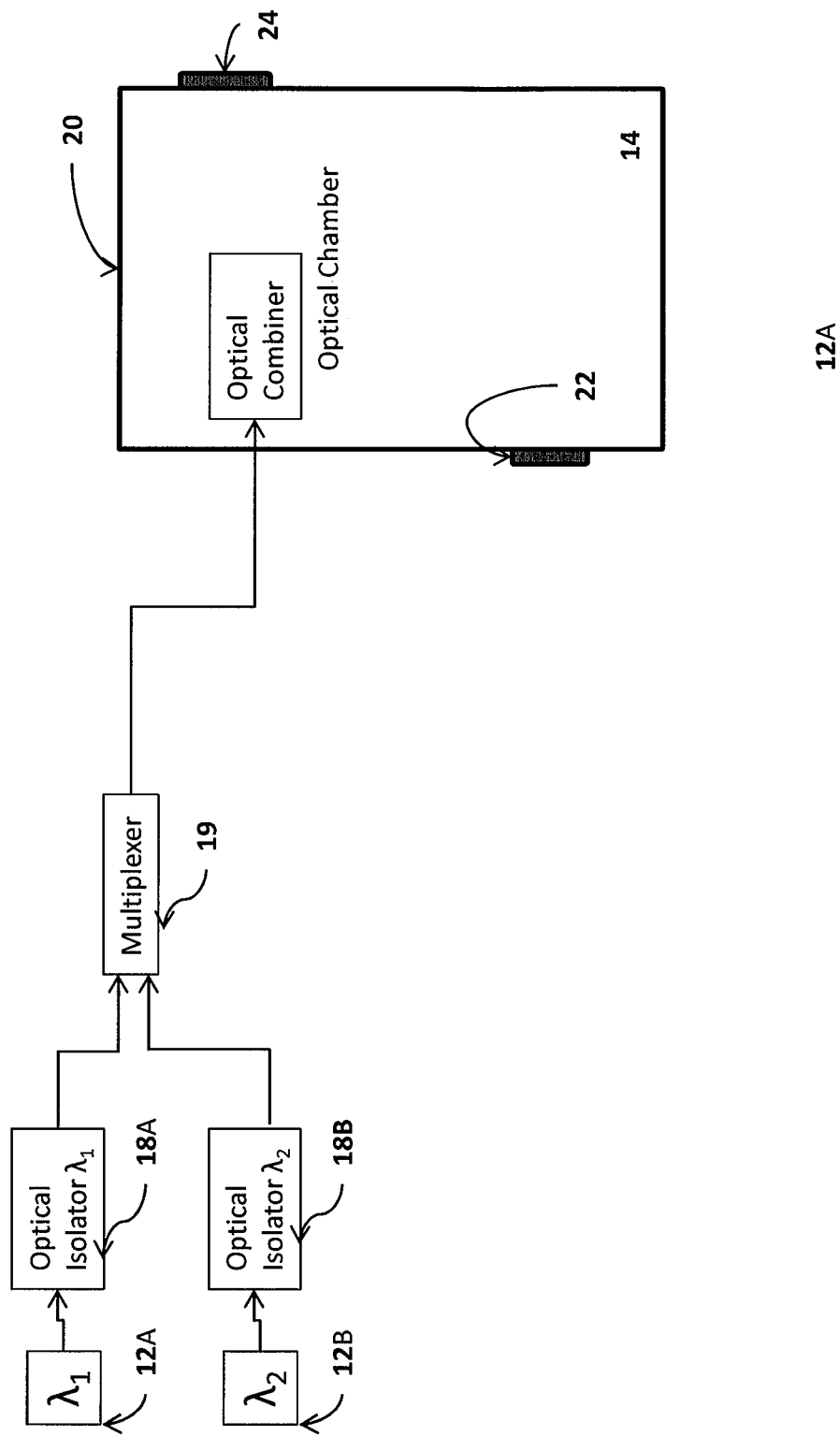
FIG. 2 is a functional block diagram generating the light emission at wavelength $\lambda_3$.

FIG. 2 is a functional block diagram generating the light emission at wavelength $\lambda_3$. Wavelength $\lambda_3$ is a mid-IR wavelength over the spectral range from about 4 μm to about 5 μm.

The first laser light source 12A emits a first beam having at the wavelength $\lambda_1$ in a range from 1500 nm to about 1650 nm. The first optical isolator 18A receives the first beam. The second laser light source 12B emits a second beam having at the wavelength $\lambda_2$ in a range from 1120 nm to about 1200 nm. The second optical isolator 18B receives the second beam. The optical selector 19, i.e. a multiplexer, is optically coupled to the first and the second optical isolators 18A, 18B via first and second polarization-maintaining optical fibers to provide a multiplexer output polarized with respect to the favorable axis associated with an optical mixer 26, e.g. non linear optical crystal. The nonlinear optical crystal 26 optically connects to the output of the multiplexer 19. This optical coupling can be done via a third polarization-maintaining optical fiber.

The first laser light source 12A may be a distributed feedback (DFB) laser having a laser gain medium periodically structured as a diffraction grating. The periodic structure of the gain medium in a DFB laser builds a one dimensional interference grating (Bragg scattering) that provides optical feedback for controlling the first laser light source. The DFB laser may have an anti-reflection coating on one end of the cavity and a high reflectivity coating on the opposite end of the cavity. Alternatively, the DFB laser may be phase-shifted DFB laser having both ends covered by anti-reflection coatings and with a phase shift in the cavity, i.e. a single quarter-wave shift at the center of the cavity or multiple smaller shifts distributed in the cavity. Alternatively, the first laser source may be a diode laser or an optical fiber laser (OFL) that includes an optical fiber doped with rare-earth elements e.g. erbium, ytterbium, neodymium, dysprosium, praseodymium, and thulium.

The second laser light source 12B may be a quantum-dot type semiconductor laser e.g. sub-watt level, highly strained InGaAs/GaAs with a free lasing wavelength at 1170 nm, that may be tuned in a range from 1147 nm to about 1197 nm. A quantum dot laser includes a layer of quantum dots as the active gain medium in its light emitting region. The quantum dot laser exhibit an electronic structure similar to atoms where the energy levels can be adjusted by controlling the quantum dot dimensions or the quantum dot material composition due to the tight confinement of charge carriers in three dimensions.

In operation, both lasers 12A, 12B are independently tunable in a controlled manner over a range of possible wavelengths. This may be achieved by single line, narrow line, or multi-band tuning. External tuning may be done by an external wavelength selector in an external cavity configuration. Internal tuning may be done by current tuning at a fixed junction temperature for a diode laser or by tuning the laser drive current at a fixed temperature.

The optical isolators 18A, 18B allow unidirectional light transmission, e.g. light transmits in only one direction while blocking light traveling in the opposite direction. Unidirectional transmission inhibits unwanted feedback into the gain medium of the respective lasers. Unwanted feedback can destabilize the frequency and/or amplitude output of the laser. The optical isolators 18A, 18B may be polarization dependent or polarization independent. Each optical isolator 18A, 18B is optimized to operate in a spectral region corresponding to the wavelength of its respective laser source. The outputs of each optical isolator 18A, 18B may be optimized to have a similar polarization state up to the point of injection into the optical combiner. The optical isolators 18A, 18B are optically coupled to be in close proximity to the emitting aperture of its respective laser source 12A, 12B.

The multiplexer 19 may be a dichroic laser mirror with significantly different reflection or transmission properties at two different wavelengths that operates to combines laser beams with different wavelengths in a know manner. To illustrate, the multiplexer 19 may reflect the first laser beam while passing the second laser beam to provide a multiplexed output directed along a common optical path toward the nonlinear optical crystal 26 or the multiplexer 19 may reflect the second laser beam and pass the first laser beam to provide a multiplexer output directed along a common optical path directed towards the non-linear optical crystal 26. Alternatively, the multiplexer 19 may be a filter-based device where the tuned wavelength is reflected off of the filter from one fiber into the output fiber and the fixed wavelength is transmitted through a dichroic laser mirror. This architecture prevents optical fringing or etaloning in the multiplexer as the laser light source is tuned in frequency. This prevents transmission intensity variations in the output power of the difference frequency laser light $\lambda_3$.

Polarization-maintaining optical fibers are optical fibers in which the polarization state of linearly-polarized light launched into the fiber is maintained during propagation, with little or no cross-coupling of optical power between the modes. The polarization-maintaining optical fibers may be optionally reinforced with a boot to relieve fiber bending stress.

Figure 3:
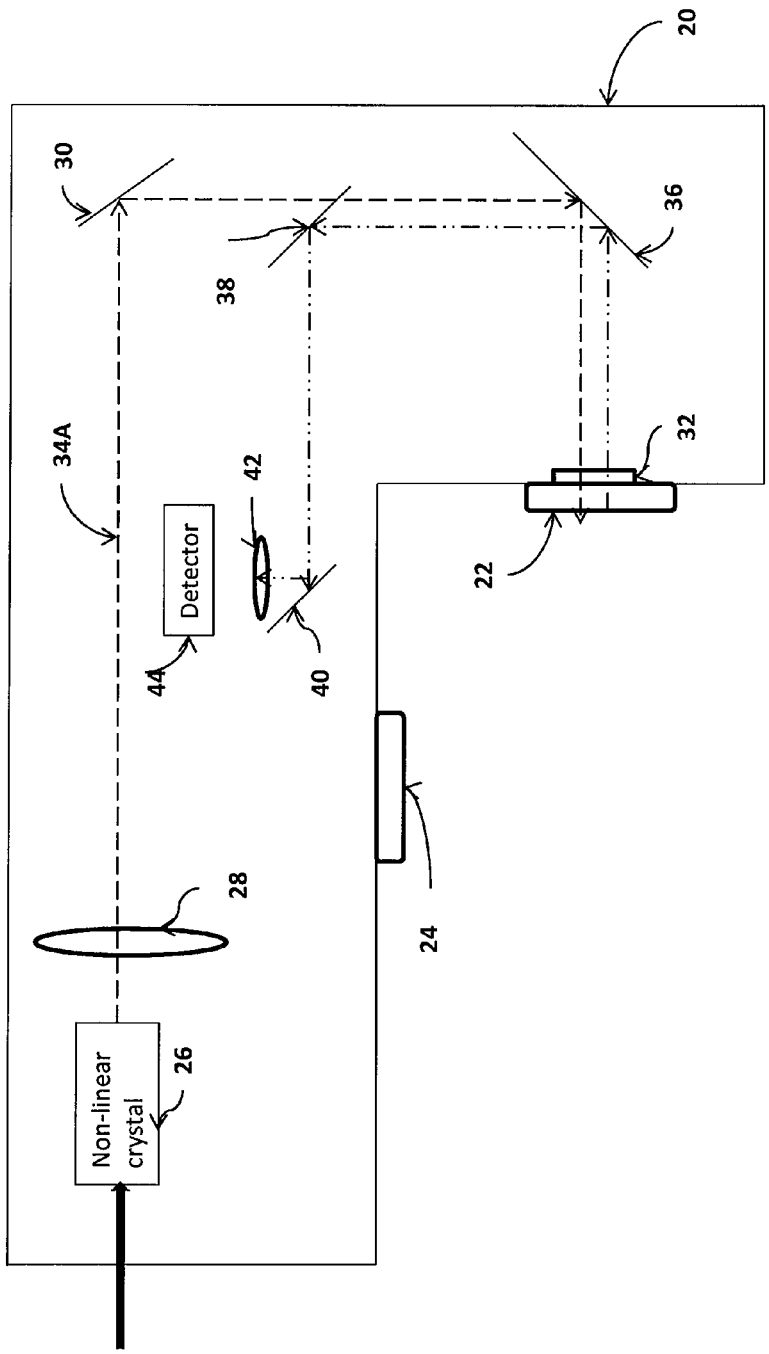
FIG. 3 is a system diagram for the optical chamber module 15 shown in FIG. 1.

FIG. 3 is a system diagram for the optical chamber module 15 shown in FIG. 1. The optical chamber module 14 performs any required conditioning or filtering of the received light and directs the received light into the gas cell 16. The first and second beams are received from the first and second optical isolators 18A, 18B. These two beams are combined within a nonlinear crystal 26. After passing through the nonlinear crystal 26, the residual light from the two laser sources is removed from the mid-infrared beam with an absorptive and/or reflective optical filter 28. A series of steering mirrors 30 directs the light at a suitable position and angle through a mid-IR transparent window.

Attenuated light returns to the optical chamber module 14 through the mid-IR transparent window 32 along a path that is slightly offset from the outgoing beam 34A (from the steering mirror 36 to the window). The slightly offset attenuated beam is further separated from the path of the outgoing beam by a pickoff mirror 38. After possible additional reflection by a turning mirror 40, the returning attenuated beam is focused by a concave mirror 42 onto a photo-detector 44. The photo-detector 44 may be any suitable detector capable of responding to mid-IR light, such as a well-known mercury-cadmium-telluride (MCT) detector.

The housing 20 of the optical chamber includes an inlet 22 and outlet 24. The inlet 22 is a gas fitting that is mated to the gas sensor cell 16 to allow the target gas of interest to flow through the cell. The target gas exits the housing through the outlet 24. The outlet 24 is connected to a vacuum pump (not shown) via a gas fitting (not shown).

Materials in the optical chamber module, e.g. machined bare aluminum, machined and anodized aluminum, copper, stainless steel screws and washers, epoxies, circuitry, wires and cables, lubricants, and greases, can be a source of numerous gases, i.e. methane, carbon monoxide, and carbon dioxide. When the optical chamber module is isolated from the gas sensor cell of FIG. 1, these background interferent gases can contribute an undesired and significant background signal to the absorption signal coming from the sample gas flowing through the gas cell.

When used in a gas sensor application, the optical chamber module 14 of FIG. 3 is no longer isolated from the gas sensor cell 16 of FIG. 1. The two volumes are connected and the sample gas flows through the gas cell and into the optical chamber module. The sample gas exits the optical chamber module through a gas fitting that connects to a vacuum pump.

The optical chamber module 14 operates at the same pressure as the gas cell and the gas in the optical chamber is now continuously flushed out by the sample gas. Thus, the background interferent gases do not built up but are flushed by the flowing sample gas. The interferent gases no longer contribute a background signal to the absorption signal.

The non-linear optical crystal may be periodically poled and configured to frequency convert the first and second laser beams. To illustrate, the periodically-poled non-linear optical crystal may achieve phase or quasi-phase matching of fundamental frequency photons and corresponding difference frequency photons through artificially structuring the material domains. The nonlinear optical crystal may be configured to output the coherent beam at a difference frequency that satisfies the mathematical relationship of $\lambda_3=(\lambda_1\lambda_2)/(\lambda_1-\lambda_2)$. The third wavelength $\lambda_3$ is in a range of about 4 μm to about 5 μm, e.g. 4.3 μm, 4.5 μm, or 4.8 μm. The third wavelength $\lambda_3$ is selected such that the wavelength coincides with a strong absorption line in the vibrational spectrum of a specific chemical species of interest.

The non-linear crystal 26 is selected such that a co-propagating light of a third wavelength, $\lambda_3$, is generated within the crystal by interaction of the electric fields of the two laser emissions with the crystal. The nonlinear optical crystal 26 may be periodically poled, and configured to frequency-convert the first and second laser beams. To illustrate, the periodically-poled nonlinear optical crystal 26 may achieve phase or quasi-phase matching of fundamental frequency photons and corresponding difference frequency photons through artificially structuring the material domains. The periodically poled nonlinear optical crystal 26 may include any of a variety of crystalline materials, such as, for example, Potassium Titanyl Phosphate (KTP), Lithium Niobate (LN), Lithium Tantalate (LT), and III-V materials. According to one embodiment, the nonlinear optical crystal is a periodically poled lithium niobate (PPLN) structure having a length in the range of about 10 to about 60 mm.

The filter 28 receives the coherent beam and removes the portions of the light at the original wavelengths $\lambda_1$, $\lambda_2$ and outputs the portion of the coherent beam characterized by the wavelength $\lambda_3$. The filter 28 is highly transmissive of the coherent light at wavelength $\lambda_3$ with low reflection at either of the front or rear filter surfaces. The filter 28 may be an optical bandpass or edge filter that transmits $\lambda_1$ and the light of wavelength $\lambda_2$. Alternatively, the filter 28 may be a piece of polished germanium (with or without a dielectric coating to enhance the reflectivity of $\lambda_1$ and $\lambda_2$), or a transmissive optical substrate with a dielectric coating on one or both surfaces to reflect the two laser source wavelengths and transmit the wavelength $\lambda_3$. The filter may also be wedged to further reduce optical fringing between the input optical face and output optical face of the filter. In this illustrative embodiment, the wedge may be from about 3° to about 5°.

The coherent beam launched from the filter 28 may be characterized by a narrow line width of less than about 10 MHz. In an illustrative embodiment, the line width of the coherent beam output of the filter may be less than about 2-3 MHz or alternatively, less than 1 MHz. The line width of the coherent beam is given as the width, i.e. the full width at half-maximum (FHWM) of the optical spectrum in term of frequency. The line width may also be expressed in terms of wave number or wavelength.

The invention claimed is:

1. An assembly comprising:
    a laser light source including:
        a first laser emitting a first laser beam having a wavelength $\lambda_1$ in a range of about 1500 nm to about 1650 nm;
        a second laser emitting a second laser beam having a wavelength $\lambda_2$ in a range of about 1120 nm to about 1200 nm;
        a first optical isolator receiving the first laser beam; and
        a second optical isolator receiving, the second laser beam;
    an optical chamber module including a housing having, an inlet and an outlet, including a mid-IR transparent window proximate the inlet, the housing including:
        a nonlinear crystal, operative to receive the first beam and the second beam, generating a third beam having a wavelength $\lambda_3$ where $\lambda_3=(\lambda_1\lambda_2)/(\lambda_1-\lambda_2)$;
        an optical filter, receiving the third beam, removing residual light related to the first and the second beam;
        a first series of steering mirrors directing the third beam through the mid-IR transparent window:
        a pickoff mirror, receiving an attenuated beam, positioned proximate the mid-IR transparent window, reflecting the attenuated beam;
        a photo-detector; and
        a second series of steering mirrors, receiving the attenuated beam and directing the attenuated beam to the photo-detector; and
    a multiplexer, interposing the first optical isolator and the non linear crystal and interposing the second optical isolator and the non linear crystal.

2. The assembly of claim 1, wherein the multiplexer reflects the first laser beam and passes the second laser beam.

3. The assembly of claim 1, further comprising:
    a first polarization maintaining optical fiber interposing the first optical isolator and the multiplexer;
    a second polarization maintaining optical fiber interposing the second optical isolator and the multiplexer; and
    a third polarization maintaining optical fiber interposing the multiplexer and the non linear optical crystal.

4. The assembly of claim 1 wherein the nonlinear optical crystal has a periodically poled structure and a length of the non linear optical crystal is 10 mm to 60 mm.

5. The assembly of claim 1, wherein the optical filter is selected from group including absorptive and reflective filters.

6. The assembly of claim 1, wherein the photo-detector is a mercury-cadmium-telluride detector.

7. The assembly of claim 1 wherein the first laser is a tunable distributed feedback diode laser.

8. The assembly of claim 1 wherein the second laser is a quantum dot semiconductor laser.

9. The assembly of claim 8 wherein the quantum dot semiconductor laser emits the wavelength $\lambda_2$ equal to about 1170 nm.

10. The assembly of claim 1 wherein the first laser emits the wavelength $\lambda_1$ in a range of about 1500 nm to about 1600 nm, the second laser emits the wavelength $\lambda_2$ in a range of about 1150 nm to about 1200 nm.

11. An assembly comprising:
    a laser light source including:
        a first laser emitting a first laser beam having a wavelength $\lambda_1$ in a range of about 1500 nm to about 1650 nm;
        a second laser emitting a second laser beam having a wavelength $\lambda_2$ in a range of about 1120 nm to about 1200 nm;
        a first optical isolator receiving the first laser beam; and
        a second optical isolator receiving the second laser beam;
    an optical chamber module including a housing having an inlet and an outlet, including a mid-IR transparent window proximate the inlet, the housing including:
        a nonlinear crystal, operative to receive the first beam and the second beam, generating a third beam having a wavelength $\lambda_3$ where $\lambda_3=(\lambda_1\lambda_2)/(\lambda_1-\lambda_2)$;
        an optical filter, receiving the third beam, removing residual light related to the first and the second beam;

a first series of steering mirrors directing the third beam through the mid-IR transparent window;

a pickoff mirror, receiving an attenuated beam, positioned proximate the mid-IR transparent window, reflecting the attenuated beam;

a photo-detector; and a second series of steering mirrors, receiving the attenuated beam and directing the attenuated beam to the photo-detector, wherein the first laser includes a first gain medium and a first output coupler operable to transmit a portion of the optical power from the first gain medium to generate the first laser beam, the first optical isolator coupled to the first output coupler at a distance within the range of about 0.01 mm to about 5 mm relative to the external surface of the first output coupler.

12. The assembly of claim 11, wherein the second laser includes a second gain medium and a second output coupler operable to transmit a portion of the optical power from the second gain medium to generate the second laser beam, the second optical isolator coupled to the second output coupler at a distance within the range of about 0.01 mm to about 5 mm relative to the external surface of the second output coupler.

13. The assembly of claim 12 further comprising an external wavelength selection element in an external cavity configuration coupled at a distance within the range of about 0.1 mm to about 5 mm to another external surface of the second optical isolator.

14. The assembly of claim 11, wherein the optical filter is selected from group including absorptive and reflective filters.

15. The assembly of claim 11, wherein the photo-detector is a mercury-cadmium-telluride detector.

16. The assembly of claim 11 wherein the first laser is a tunable distributed feedback diode laser.

17. The assembly of claim 11 wherein the second laser is a quantum dot semiconductor laser.

18. The assembly of claim 17 wherein the quantum dot semiconductor laser emits the wavelength $\lambda_2$ equal to about 1170 nm.

19. The assembly of claim 11 wherein the first laser emits the wavelength $\lambda_1$ in a range of about 1500 nm to about 1600 nm, the second laser emits the wavelength $\lambda_2$ in a range of about 1150 nm to about 1200 nm.

20. The assembly of claim 11 wherein the nonlinear optical crystal has a periodically poled structure and a length of the non linear optical crystal is 10 mm to 60 mm.

21. The assembly of claim 11, further comprising:
a multiplexer, interposing the first optical isolator and the non linear crystal and interposing the second optical isolator and the non linear crystal.

* * * * *